(12) United States Patent
Chaiken et al.

(10) Patent No.: US 6,681,133 B2
(45) Date of Patent: Jan. 20, 2004

(54) METHODS AND APPARATUS FOR OBTAINING ENHANCED SPECTROSCOPIC INFORMATION FROM LIVING TISSUE

(75) Inventors: Joseph Chaiken, Fayetteville, NY (US); Charles M. Peterson, Potomac, MD (US); Karen P. Peterson, Potomac, MD (US)

(73) Assignee: LighTouch Medical, Inc., New Hope, PA (US)

( * ) Notice: Subject to any disclaimer, the term of this patent is extended or adjusted under 35 U.S.C. 154(b) by 106 days.

(21) Appl. No.: 09/998,036

(22) Filed: Nov. 30, 2001

(65) Prior Publication Data

US 2002/0091322 A1 Jul. 11, 2002

Related U.S. Application Data

(62) Division of application No. 09/456,020, filed on Dec. 3, 1999, now Pat. No. 6,352,502.
(60) Provisional application No. 60/110,764, filed on Dec. 3, 1998.

(51) Int. Cl.[7] .................................................. A61B 6/00
(52) U.S. Cl. ........................ 600/473; 372/34; 372/29.02
(58) Field of Search .................................. 600/473, 475, 600/476; 607/88, 89; 356/300, 301, 302, 923; 359/196

(56) References Cited

U.S. PATENT DOCUMENTS

| | | |
|---|---|---|
| 3,906,241 A | 9/1975 | Thompson |
| 4,427,889 A | 1/1984 | Müller |
| 4,655,225 A | 4/1987 | Dähne et al. |
| 4,975,581 A | 12/1990 | Robinson et al. |
| 5,086,229 A | 2/1992 | Rosenthal et al. |
| 5,194,913 A | 3/1993 | Myrick et al. |
| 5,243,983 A | 9/1993 | Tarr et al. |
| 5,261,410 A | 11/1993 | Alfano et al. |
| 5,305,759 A | 4/1994 | Kaneko et al. |

(List continued on next page.)

FOREIGN PATENT DOCUMENTS

| | | |
|---|---|---|
| EP | 0 875 201 A1 | 11/1998 |
| WO | WO 93/00856 | 1/1993 |
| WO | WO 96/03074 | 2/1996 |
| WO | WO 97/15226 | 5/1997 |
| WO | WO 98/38907 | 9/1998 |
| WO | WO 00/02479 | 1/2000 |

OTHER PUBLICATIONS

Anderson, R. Rox et al., (1981) "The Optics of Human Skin," The Journal of Investigative Dermatology, 77(13):13–19.

(List continued on next page.)

*Primary Examiner*—Dennis Ruhl
*Assistant Examiner*—Runa Shah Qaderi
(74) *Attorney, Agent, or Firm*—Gates & Cooper, LLP (57) ABSTRACT

Disclosed is a method for obtaining feedback to drive a servo system for aligning and maintaining alignment in optical systems that bring light to an in vivo skin sample, for adjusting the focus of the optical system, and for adjusting the net depth of focus of the optical system within the in vivo system under characterization. These methods comprise adjusting the angle of incidence of electromagnetic radiation and/or providing a shielding lens to block scattered incident light, or otherwise limiting the field of view of the Raman scattered radiation collection system to exclude optical surfaces of the excitation delivery portion of the optical system. In one embodiment, the method comprises discriminating between Raman signals originating on outer portions of skin from signals originating from substances deeper within the skin or other tissues. In another embodiment, the invention provides a method for detecting skin abnormalities and for assessing the aging of skin and related tissues.

12 Claims, 5 Drawing Sheets

U.S. PATENT DOCUMENTS

| | | | |
|---|---|---|---|
| 5,372,135 A | | 12/1994 | Mendelson et al. |
| 5,553,616 A | | 9/1996 | Ham et al. |
| 5,680,410 A | * | 10/1997 | Kim et al. .................... 372/34 |
| 5,713,364 A | | 2/1998 | DeBaryshe et al. |
| 5,813,987 A | | 9/1998 | Modell et al. |
| 5,995,867 A | | 11/1999 | Zavislan et al. |
| 6,181,718 B1 | * | 1/2001 | Kobayashi et al. ........... 372/34 |

OTHER PUBLICATIONS

E.A. Carter et al. (1998) SPIE 3257:72–77.

H.G.M. Edwards et al. (1996) Chemistry in Australia pp. 454–455.

H.G.M. Edwards et al. (1995) Journal of Molecular Structure 347:379–387.

E.E. Lawson et al. (1997) Journal of Raman Spectroscopy 28:111–117.

M. Rajadhyaksha et al. (1995) The Society for Investigative Dermatology p. 946.

A.T. Tu (1982) Raman Spectroscopy in Biology, John Wiley & Sons, NY pp. 134–149.

K.G. Brown et al. (1973) Biochem. Biophys. Res. Commun. 54:358–364.

K. Larsson (1973) Chem. Phys. Lipids 10:165–176.

R. Mendelsohn (1973) Nature 243:22–24.

* cited by examiner

METHODS AND APPARATUS FOR OBTAINING ENHANCED SPECTROSCOPIC INFORMATION FROM LIVING TISSUE

This application is a Divisional of application Ser. No. 09/456,020, now U.S. Pat. No. 6,352,502 filed Dec. 3, 1999, entitled "METHODS FOR OBTAINING ENHANCED SPECTROSCOPIC INFORMATION FROM LIVING TISSUE, NONINVASIVE ASSESSMENT OF SKIN CONDITION AND DETECTION OF SKIN ABNORMALITIES", which application is incorporated herein by reference.

This application claims the benefit of U.S. provisional patent application Ser. No. 60/110,764, filed Dec. 03, 1998, the entire contents of which are incorporated herein by reference. Throughout this application, various publications are referenced. These publications are incorporated herein by reference in order to describe more fully the state of the art to which the invention pertains.

TECHNICAL FIELD OF INVENTION

The invention relates to a method and apparatus for qualitative or quantitative noninvasive assessment of the metabolic and structural components of skin and nearby tissues using Raman spectroscopy. The invention relates to maintaining depth and position of focus of a Raman excitation source, regardless of whether an imaging light collection system is used. This system also provides first order servo correction for automatic focusing of an imaging system. The invention additionally relates to identifying spectroscopic depth markers in tissues, and to detecting skin abnormalities and assessing the aging of skin and related tissues.

BACKGROUND OF THE INVENTION

There has always been a need for reliable and precise quantitative methods and associated apparatus for diagnosing medical abnormalities and for assessing the general condition of body tissues. While any approach that offers early and reliable warning of medical problems has some utility, noninvasive methods offer many advantages. Anticipation by a patient of pain and scarring associated with invasive procedures can cause delays in seeking medical attention. There is also a myriad of inconveniences, risks and difficulties associated with direct collection and contact with patient body fluids. For these reasons, there has been intense scientific and engineering research into devising noninvasive approaches to assessment and diagnosis of medical conditions.

Use of spectroscopic methods, while of considerable use in direct in vitro application to fluids, has not found equal in vivo application. In vivo sampling is substantially more complicated for a variety of reasons, although some of the challenges can be handled by reference to in vitro procedures. First, even in vitro procedures require at least some sample preparation before spectroscopic interrogation. But in vivo samples cannot be handled with nearly the ease of in vitro samples. All chemometric analyses benefit from the availability of samples having known composition of various analytes. Selectively modulated in vitro samples are much easier to synthesize or otherwise obtain than in vivo samples. Thus, samples for chemometric interpretation of in vivo samples can be expected to require specialized approaches to sample preparation and specifically designed methods for obtaining modulated samples of known composition. Long data collection times are needed to extract small signals from some samples, but in vivo sampling requires the patient to endure the waiting. Prolonged data collection is not always practical. Moreover, applying too much excitation light to in vivo samples can lead to catastrophic results.

Noninvasive in vivo chemical analysis of human and animal tissues has long been a goal of chemists and the medical community. Blood oximetry is an example of a noninvasive form of analysis that is now ubiquitous in intensive care and other situations. Noninvasive techniques involve contacting the tissue in question with some form of electromagnetic radiation, and detecting the effect of the contact on the radiation. The frequency range of the radiation and the choice of tissue to contact, determines the type of structural, concentration or other physico-chemical information that is available.

The optics of human skin have been extensively reviewed. The interaction with visible light contacting blood in the capillary beds just beneath the epidermis of human skin can be exploited to estimate the oxygen content of blood, thereby giving a quantitative measure of the condition of the patient's respiratory and cardiovascular systems, i.e. blood oximetry. The present invention is directed to assessing the condition of the skin at the molecular and supramolecular scale, making vibrational spectroscopy an ideal probe.

SUMMARY OF THE INVENTION

The invention provides a method and apparatus for obtaining feedback to drive a servo system for aligning and maintaining alignment in optical systems that bring light to an in vivo skin sample, for adjusting the focus of the optical system, for adjusting the net depth of focus of the optical system within the in vivo system under characterization, and for driving a tissue-directed search and mapping algorithm. The invention additionally provides a method and apparatus for obtaining feedback to drive a servo system for aligning and maintaining alignment in optical systems that collect light from an in vivo skin sample, and for adjusting the focus of the optical system. These methods comprise adjusting the angle of incidence of electromagnetic radiation and/or providing a shielding lens to block scattered incident light, or otherwise limiting the field of view of the Raman scattered radiation collection system to exclude optical surfaces of the excitation delivery portion of the optical system.

Also provided is a method and apparatus for identifying spectroscopic depth markers in tissues. In one embodiment, the method comprises discriminating between Raman signals originating on outer portions of skin from signals originating from substances deeper within the skin or other tissues. In some embodiments, these methods comprise selecting optics for Raman detection to maximize one or more Raman features corresponding to lipids and proteins of the skin.

The invention provides a method and apparatus for obtaining spectroscopic information from living tissue of a subject. In one embodiment, the method comprises irradiating a tissue of interest in a subject with light having an excitation wavelength and that passes from a light source through a first adjustable lens, and passing spectra that are emitted by the tissue through a second adjustable lens. The spectra that are passed through the second adjustable lens are then collected and analyzed to determine a target signal associated with an analyte of interest. The method further comprises deriving a correction signal from the target signal, and adjusting the position of the first adjustable lens or the second adjustable lens on the basis of the correction signal so as to enhance the target signal. In a preferred embodiment, the spectra are Raman spectra. The method can optionally further comprise selectively dispersing a target wavelength of the collected spectra prior to analyzing the collected spectra. Preferably, the dispersing comprises filtering out wavelengths other than the target wavelength, or passing the collected spectra through a spectrograph.

In another aspect, the invention provides a non-invasive method and apparatus for spectroscopically probing and mapping a target layer of skin in a subject. The method comprises irradiating a target layer of skin in a subject with light having an excitation wavelength that passes from a light source through a first adjustable lens, passing spectra that are emitted by the tissue through a second adjustable lens, and collecting spectra that are passed through the second adjustable lens. The method further comprises analyzing the collected spectra to determine a target signal associated with the target layer of skin, and adjusting the position of the first adjustable lens or the second adjustable lens so as to increase the target signal. Optionally, the method further comprises deriving a correction signal from the target signal and relaying the correction signal to the first adjustable lens or to the second adjustable lens, wherein the correction signal effects an adjustment of the first adjustable lens or the second adjustable lens. In one embodiment, the method and apparatus include an adjustable aperture, such as one or more irises, as in a confocal microscope, positioned between the skin and the light collection system. A correction signal derived from the target signal is then used as feedback to the adjustable aperture to optimize the collection of spectra from the target layer of skin.

In another aspect, the invention provides a method and apparatus for spatial mapping and detecting abnormalities in living tissue of a subject. The method comprises irradiating a tissue of interest in a subject with light having an excitation wavelength and that passes from a light source through a first adjustable lens, passing spectra that are emitted by the tissue through a second adjustable lens, and collecting spectra that are passed through the second adjustable lens. The method further comprises analyzing the collected spectra to determine a target signal associated with a tissue feature indicative of an abnormality, deriving a correction signal from the target signal, and adjusting the position of the first adjustable lens or the second adjustable lens on the basis of the correction signal so as to enhance the target signal. In one embodiment, the tissue of interest comprises skin. Other examples of tissues of interest include, but are not limited to, stratum corneum, epidermis, intradermal capillary beds, and dermis.

The invention further provides a method and apparatus for stabilizing a wavelength and/or amplitude of light emitted by a diode laser. The method comprises irradiating a specimen with excitation light from the diode laser, and collecting Raman spectra at a target wavelength emitted by the irradiated specimen, wherein the target wavelength is associated with a strong feature in the specimen. In one embodiment, the target wavelength is associated with silica, as present in the optical path, such that an optical element within the system serves as the irradiated specimen. The target wavelength associated with silica is a wavenumber shift of about 1003 $cm^{-1}$ from the excitation wavelength. The method further comprises determining a quantity of spectra emitted at the target wavelength, relaying to the diode laser a signal proportional to the determined quantity, and regulating the temperature of the diode laser so as to maintain a maximal spectra emitted at the target wavelength.

In another embodiment, Raman spectra are collected at two or more wavelengths: at least one positive target wavelength associated with a strong feature in the specimen, and at least one a negative target wavelength associated with a weak feature in the specimen. The method further comprises determining a quantitative difference between the spectra emitted at the positive target wavelength and the spectra emitted at the negative target wavelength, relaying to the diode laser a signal proportional to the determined difference, and regulating the temperature of the diode laser so as to maintain a maximal difference between the spectra emitted at the positive target wavelength and the spectra emitted at the negative target wavelength. In a preferred embodiment, the specimen is skin, the positive target wavelength is a wavenumber shift of about 2940 or 1665 $cm^{-1}$ from the excitation wavelength and the negative target wavelength is a wavenumber shift of about 2800 or 1775 $cm^{-1}$, respectively, from the excitation wavelength.

The method can be performed non-invasively on living tissue. Optionally, the method further comprises adjusting the position of a first adjustable lens located in the optical path of the excitation light so as to increase the determined quantity of the spectra emitted at the target wavelength, or the difference between the spectra emitted at the positive target wavelength and the spectra emitted at the negative target wavelength, and/or likewise adjusting the position of a second adjustable lens located in the optical path of the emitted spectra so as to increase the determined quantity of spectra or difference between the spectra emitted at the positive target wavelength and the spectra emitted at the negative target wavelength.

In another embodiment, the invention provides a method and apparatus for assessing the aging of skin and related tissues. The method comprises characterizing the content of the skin using Raman spectroscopy as described above. The aging of skin is related to morphological changes in the tissues on a spatial scale of 10–10,000 microns which can be mapped at very early stages of their development using the method of this invention. These morphological changes, i.e. wrinkles, may or may not be associated with chemical variations. These changes are purely physical and may be precisely mapped using the method of the invention. In one embodiment, the collagen, elastin, and/or keratin content of the skin is characterized. In another embodiment, the size and location of fat deposits is characterized.

In another aspect, the invention provides an apparatus for enhancing spectroscopic information obtained from living tissue of a subject. The apparatus comprises a signal analyzer adapted to receive input from a detector and a processor connected to the signal analyzer, wherein the processor is capable of producing an output signal that is proportional to a quantity of Raman spectra received by the signal analyzer from the detector. The output signal can be directed to a diode laser for regulating the temperature of the diode laser, thereby stabilizing the wavelength and/or amplitude of light emitted by the diode laser and focused onto the living tissue to be spectroscopically probed. The output signal can also be directed to an adjustable lens, either a first adjustable lens used to focus the light onto the living tissue, or a second adjustable lens used to collect Raman spectra scattered by the living tissue.

Alternatively, the output signal can be directed to an adjustable aperture, such as an iris in a confocal microscope. The adjustable aperture can be coupled to an electronically controlled translation stage that is connected to the processor and optically aligned with an input path to the detector, wherein the output signal regulates movement or diameter of the adjustable aperture along or perpendicular to an optical axis aligned with the input path of the detector. The apparatus provides a feedback system for optimizing the quality and the focusing of the spectroscopic system, and provides connections between data processors and translation stages that control the positions of optical elements in a device.

DETAILED DESCRIPTION

The method and apparatus described herein allow detection of molecular "fingerprints" associated with various structural and metabolic components of the skin and nearby tissues via non-invasive spectroscopy. In some cases such "fingerprints" reveal abnormalities of the skin. Such fingerprints will often be useful in revealing the general condition of skin. The method provides for quantitation of moisture content, total callus content as well as protein, lipid and carbohydrate content. In one embodiment, collagen, α-keratin, β-keratin, elastin, mucopolysaccharides, neutral lipids, polar lipids, ceramides, and/or cholesterol sulfate are assessed. The degree of skin oxidation and protein cross-linking via disulfide, linkages can also be assessed.

The method of the invention also provides for using the detected spectra to feedback and regulate the output of the light source as well as to regulate the positioning of focusing and collecting lenses, and the positioning of an iris in a confocal microscope. This feedback system allows the method to be performed with simpler, less expensive lasers, and without requiring the use of fiber optics. Not only does the invention avoid the need for lasers having elaborate and expensive temperature regulating systems, it also avoids the need for more complicated and expensive feedback systems for adjusting the focus of the apparatus. The apparatus of the invention removes unwanted incident light and sets the focal plane via filtering and simple electronics. Because the feedback system of the invention relies on chemical information rather than image data, it does not require use of a CCD camera, for example, in the feedback loop.

The method also allows for adjustments to accommodate movement by the subject. In addition, the method and apparatus of the invention can be used in combination with other techniques, such as magnetic resonance imaging (MRI), confocal optics, and the use of chemical markers or labels (e.g., deuterium). Moreover, combination of the method with MRI can be done without introducing metal.

Definitions

All scientific and technical terms used in this application have meanings commonly used in the art unless otherwise specified. As used in this application, the following words or phrases have the meanings specified.

As used herein, "Raman spectra associated with" a given component refers to those emitted Raman spectra that one skilled in the art would attribute to that component. One can determine which Raman spectra are attributable to a given component by irradiating that component in a relatively pure form, and collecting and analyzing the Raman spectra emitted by the component in the relative absence of other components. Those skilled in the art are aware of available libraries that catalog known Raman spectra.

As used herein, to "enhance a target signal" means to increase the quantity or quality of a target signal having a wavelength associated with an analyte of interest relative to the quantity or quality of a non-target signal having a wavelength not associated with the analyte of interest.

As used herein, a "strong" feature is a Raman feature that results in one scattered wavelength-shifted photon per $10^4$–$10^6$ incident excitation photons. Where the Raman features have been resonance enhanced or surface enhanced, strong features can result in one scattered wavelength-shifted photon per $10^3$–$10^6$ incident excitation photons.

As used herein, a "weak" feature is a Raman feature that results in one scattered wavelength-shifted photon per $10^8$–$10^9$ incident excitation photons.

As used herein, "wavelength dispersion" means spatially separating signals of individual wavelengths within a group of wavelengths. Such dispersion can be achieved with, for example, a spectrograph or use of one or more filters.

As used herein, "tissue" means any portion of an organ or system of the body, including, but not limited to, skin, capillary beds, blood, muscle, breast and brain.

As used herein, unless context clearly indicates otherwise, "a" or "an" means at least one, and can include a plurality.

The invention described herein is based on the discovery that Raman scattering can be used noninvasively to obtain quantitative information concerning skin and nearby tissues. As disclosed herein, the methods and apparatus used to obtain Raman spectroscopic data can be adapted for application to skin and other in vivo samples. This intradermal excitation provides an objective approach to skin characterization.

Raman Spectroscopy of Skin

To perform absorption based vibrational spectroscopy, the use of infrared radiation to obtain quantitative information is limited by the transmission properties of the tissue. There is considerable Mie scattering, spatial inhomogeneity, and tortuous interfaces permeating tissues and organs, making quantitation of path length problematic and complicating, if not invalidating, the applicability of Beer's Law. Moreover, absorption limits the amount of light that can be employed. The availability of adequate infrared lasers or adequate incoherent light sources is limited. Optical contact with the skin or other tissue can be made using either waveguide, i.e. evanescent wave, or direct contact.

In large part, moisture content of a naturally hydrated biomembrane, such as stratum corneum, makes direct infrared absorption/reflectance spectroscopy problematic, i.e. difficult to execute reproducibly, regardless of how the light contacts the skin. For example, stratum corneum is typically about 10 $\mu$m thick, but can swell to several times that thickness when wet. This variation in density affects light propagation in a way that poses nonlinearity problems. Raman spectroscopy, on the other hand, is much less affected by water, and so is often the method of choice for wet samples.

On the other hand, Raman scattering is a comparatively weak process and, given the peculiar optical properties of human tissue, a novel approach is required to actually obtain meaningful in vivo spectra. There must be control of blood flow, or some type of compensation in the data analysis for whatever form of tissue modulation is employed. Local pressure and temperature can have a dramatic effect on the blood volume of the intersection between the irradiation zone and the collection zone.

Described herein is a system to maintain focus of the combined excitation and collection systems at the desired position on or within the skin or surrounding tissues. To this end, an approach has been devised to allow a nonimaging optical system to establish a feedback loop and thereby a servo system for maintaining the position and the depth of focus of the Raman excitation source as the sample is moved. The same approach can work equally well to maintain the optimal configuration of the light collection system as well.

The method disclosed herein allows such spectroscopic data to be collected with greater efficiency, greater selectivity, and ultimately, higher signal to noise. Contrary to the teachings of other processes, real lasers lack the spectral purity required to forego the need for extensive blocking of the Rayleigh scattered light from the Raman detector. Raman scattering is actually quite weak when not resonance enhanced, and adequately shielding the detector from the blinding effects of the incident light is required to observe quantitative results from in vivo Raman scattering and utilize the full dynamic range of any detector.

Part of the necessary blocking can be achieved by contacting the skin with the laser light at an appropriate angle and by properly orienting the observation system. The remaining reduction can be achieved by specifying that there can be no optical surface of the excitation delivery part of the optical system that is within the direct field of view of the Raman scattered radiation collection system. The field of view is designated such that it does not include objects visible because of light reflected from the skin surface.

The methods and apparatus disclosed herein overcome the challenges presented by spectroscopic probing of in vivo tissues by providing for regulation of lens and aperture positions and excitation wavelength output. Target spectra for obtaining information about skin and tissue contents have been identified in the literature. Edwards et al., 1995, J. Molecular Structure 347:379–388; and Carter et al., 1998, SPIE 3257:72–77, describe Raman features of interest to dermatological diagnostics. Lawson et al., 1997, J. Raman Spectroscopy 28:111–117 describes Raman spectra associated with cancers, tumors, DNA, stratum corneum, hair and nails. Tu, 1982, Raman Spectroscopy in Biology: Principles and Applications, Chap. 5:134–149, describes Raman features associated with nucleic acids and inorganic phosphate.

Spectroscopic Depth Markers

Beyond the considerations noted above, there is a need for spatial stability in the excitation and light collection systems. The structure of the stratum corneum, epidermis, and dermis layers has a chemical and physical complexity on a spatial scale of tens to hundreds of microns. Wrinkles represent physical complexities on a larger scale. Failure to fully consider this compositional and physical heterogeneity leads to an inability to distinguish between the sources of the vibrational spectroscopic signals. It is therefore desirable to identify and utilize inherent spectroscopic depth markers. This overcomes difficulties in obtaining adequate contrast, which is a limiting factor in the use of standard in vivo scanning confocal microscopy of human skin (Rajadhyaksha et al., 1995, J. Invest. Derm. 104(6) :946–952).

It is known that there is a strong Raman feature centered near 3000 $cm^{-1}$ corresponding to the —C—H stretching motions of the lipids and proteins in the skin. This feature is sufficiently removed from the Rayleigh line that it can be utilized for the depth marking purpose mentioned above. Other features known to be associated with epidermis, dermis, sub dermal fat or capillary beds can be used as depth markers. For example, more information associated with a particular analyte found in the epidermis than in deeper layers suggests that the subject acquired the analyte via touch. In contrast, higher levels of analyte associated with subdermal fat than with epidermis would be indicative of acquiring the analyte by ingestion.

Using a simple filter to isolate the signal from other Raman/fluorescence/source contamination (e.g. unwanted amplified spontaneous emission (ASE)), the excitation system focusing optics can provide this signal to a microprocessor to provide feedback for servo control. In one embodiment, a graph of total Raman (inelastic) light scattered shows that this observable measure is sensitive to the position of the excitation focusing and so filtering can be used for signal isolation. In another embodiment, the optics can be adjusted to maximize the entire 3000 $cm^{-1}$ Raman feature. This provides a first order method for optimizing the parameters of the light collection and excitation systems.

The shape of this same Raman feature varies with depth below the stratum corneum. The composition of the 3000 $cm^{-1}$ Raman feature varies with composition, and so can be used to lock onto a particular depth of focus for the excitation and/or for the collection optics. The greater the depth, the more the Raman feature is composed of longer Raman shifts. There are also other Raman features between 1000–1800 $cm^{-1}$ that can be equally useful for obtaining depth information.

Apparatus

Figure 1:
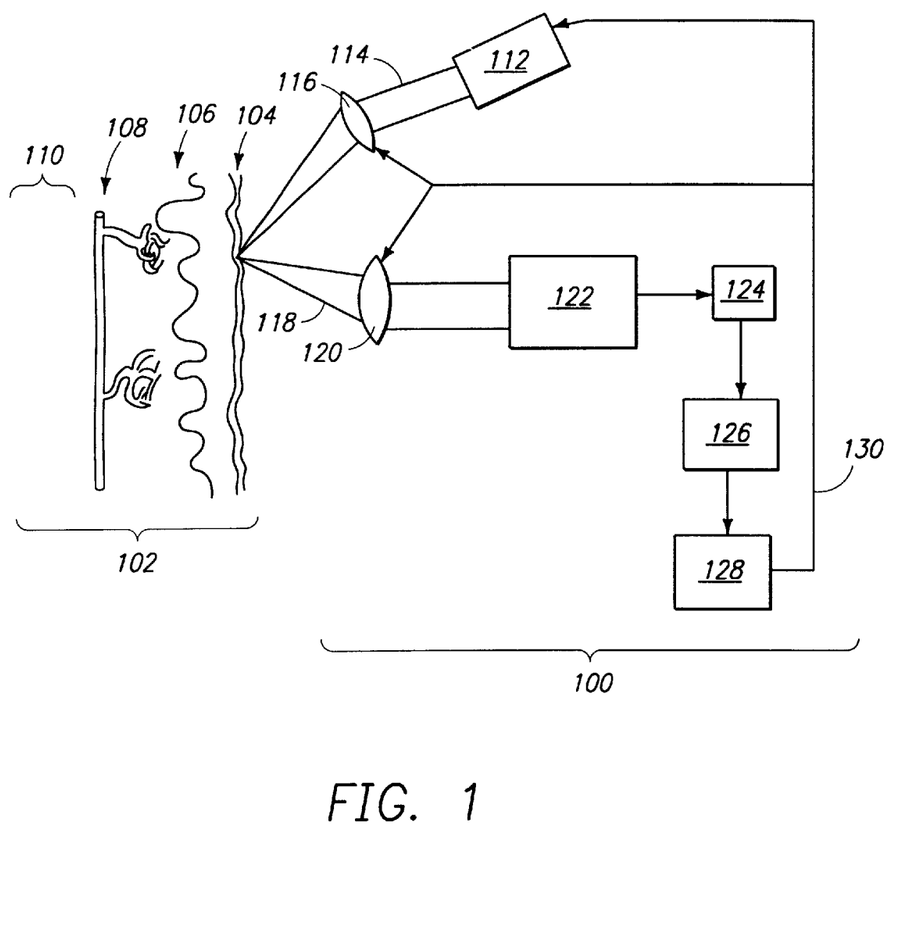
FIG. 1 is a schematic illustration of an apparatus 100 for use in accordance with one embodiment of the invention for spectroscopic probing of skin 102.
Figure 2:
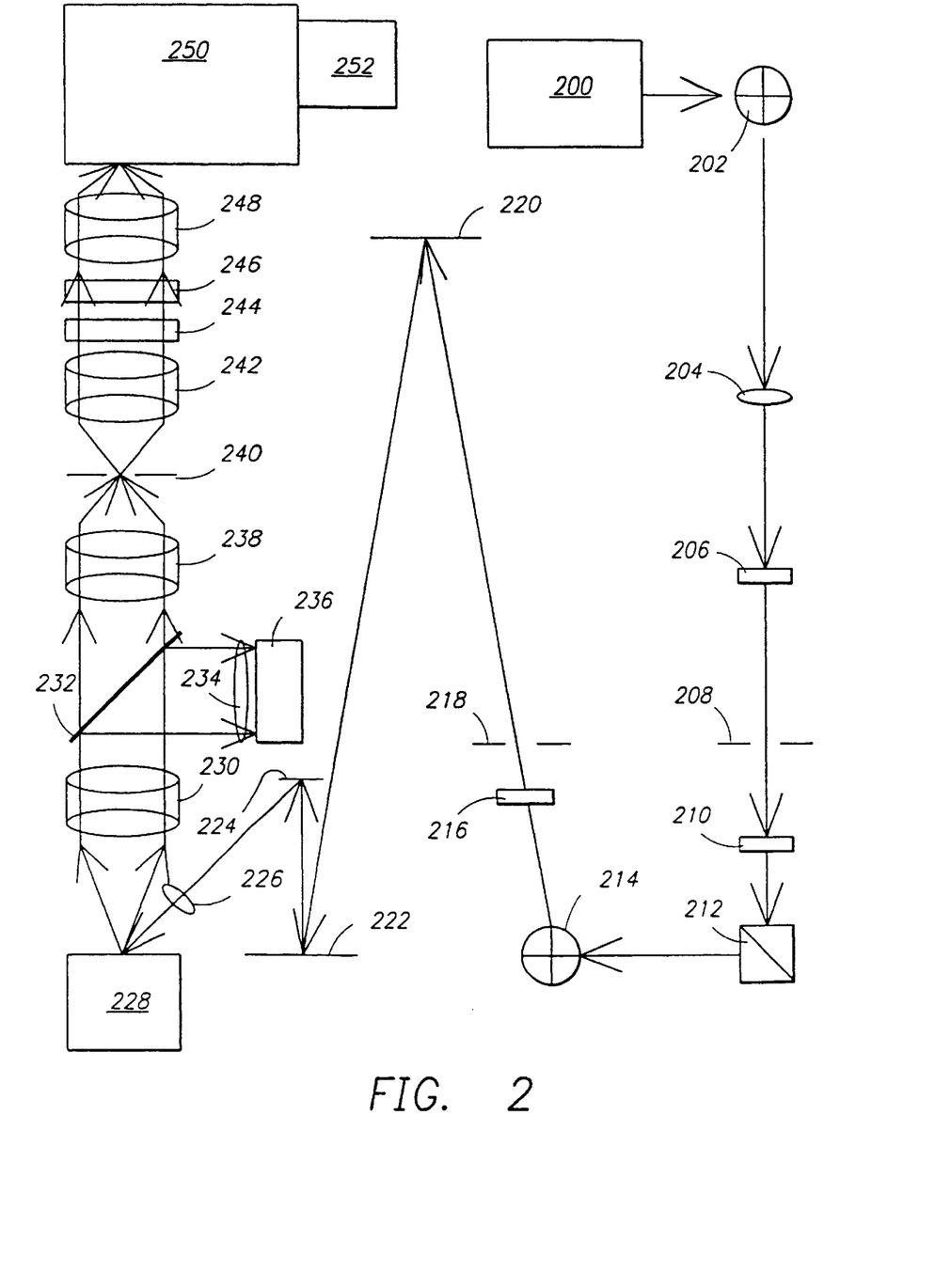
FIG. 2 is a schematic representation of a simple confocal, four-lens system for combining depth discrimination with spectroscopy.

FIG. 1 is a schematic illustration of an apparatus 100 for use in accordance with one embodiment of the invention for spectroscopic probing of skin 102. The apparatus 100 can be directed at the stratum corneum 104 at the skin 102 surface, or at progressively deeper layers, including epidermis 106, capillary beds 108 and dermis 110. A laser 112 emits excitation light along an optical path 114 that is focused onto the skin 102 via a first adjustable lens 116. Scattered light emitted by the skin 100 travels along an optical path 118 through a second adjustable lens 120 to a wavelength dispersion element 122. Wavelengths of light passing through the dispersion element 122 are converted to electronic signals by a detector 124, the output of which goes to a signal analyzer 126 and then to a processor 128 that derives a correction signal 130 that returns to the laser 112, the first adjustable lens 116, the second adjustable lens 120 and/or an adjustable aperture 240, as shown in FIG. 2. The correction signal 130 can relate to, for example, wavelength, spatial orientation, alignment of optical elements and/or depth selection. Motorized translation stages and controllers, such as the Newport 860-C2 controller and the 860A drive (Newport Inc., Irvine, Calif.), can be easily integrated into closed loop applications for adjusting position of lenses 116, 120 and apertures 240.

The laser 112 can be a 785 nm, amplitude and wavelength stabilized, external cavity, CW laser 500, (SDL XC-30; SDL Inc., San Jose, Calif.) or similar laser such as a PI-ECL-785-1000FHP (Process Instruments, Inc., Salt Lake City, Utah), producing a maximum total power of 300–700 mW. In the case of the SDL laser, more than half of this power is associated with a large, spectrally wide and unsymmetrical base of amplified spontaneous emissions (ASE). This is adequate to obtain Raman spectra of simple, less challenging samples, i.e. virtually any in vitro sample. To obtain acceptable in vivo spectra, however, a substantial amount of the ASE should be removed. This is done using a holographic bandpass filter (Kaiser Optical Systems, Ann Arbor, Mich.). While this does not remove all of the disturbing background radiation, it is adequate to allow in vivo spectra to be obtained. Alternatively, ASE can be removed by using a dielectric filter (Omega Optical, Brattleboro, Vt.; CVI, Tucson, Ariz.). The Process Instruments laser contains much less ASE, and so a dielectric filter is adequate to allow in vivo Raman signals to be observed.

Optics for correcting the spatial arrangement of the fast and slow axes of the laser divergence, as well as for obtaining the optimum polarization for diffraction efficiency and background reduction in the f1.4 holographic spectrograph 122 eventually allow us to bring only about 500–300 mW of laser power to the sample 102. The spectrograph 122 can be a Holospec (Kaiser Optical Systems, Ann Arbor, Mich.) or other available spectrograph (e.g., from Process Instruments, Salt Lake City, Utah). All optics are antireflection coated for 785 nm and a 13 cm focal length lens 116 is used to finally bring the light to the tissue 102 in question. An angle of incidence of approximately 53° gives acceptable results.

The light collection system uses two 50 mm f1.4 Nikon camera lenses, a holographic notch filter (Kaiser Optical Systems, Ann Arbor, Mich.) and a Polacor™ (Corning) polarizer to bring the scattered light from the sample 102 to the entrance of the spectrograph 122. Alternatively, properly anti-reflection-coated (performed by CVI, Tucson, Ariz.) high purity fused silica single element lenses (Corning HPFS 7940 or 7980, Corning, N.Y.) can be used in place of camera lenses, with the benefit of increasing total throughput and reducing a large amount of unwanted fluorescence from optical elements.

The detection system 124 is an IR enhanced, liquid nitrogen cooled CCD array (LN/CCD-1024-EHRB/1, Princeton Instruments, Inc., Trenton, N.J.). The resolution of the spectrograph system is 6 cm$^{-1}$ with wavenumber accuracy of 6 cm$^-$ using a calibration based on known lines in atomic emission spectra. Standard computer equipment can be used for the signal analyzer 126 and processor 128 (e.g., parallel, serial, interface cards, A/D and D/A converters).

The invention provides an apparatus for enhancing spectroscopic information obtained from living tissue of a subject, and for searching for and mapping specific types of tissue. The apparatus comprises a signal analyzer adapted to receive input from a detector and a processor connected to the signal analyzer, wherein the processor is capable of producing an output signal that is proportional to a quantity of Raman spectra received by the signal analyzer from the detector. The output signal can be directed to a diode laser for regulating the temperature of the diode laser, thereby stabilizing the wavelength and/or amplitude of light emitted by the diode laser and focused onto the living tissue to be spectroscopically probed. The output signal can also be directed to an adjustable lens aperture, either a first adjustable lens used to focus the light onto the living tissue, or a second adjustable lens or an adjustable aperture used to collect Raman spectra scattered by the living tissue. The apparatus provides a feedback system for optimizing the quality and the focusing of the spectroscopic system.

FIG. 2 shows a schematic representation of a confocal, four-lens system adapted for depth discrimination. Such a system can be used to determine the depth of a signal emitted by tissue that is spectroscopically probed. Determination of the depth of a source of emitted light permits identification of the type of tissue, e.g., skin, blood, and of the type of lipid, e.g., lipid, phospholipid, sphingolipid. In particular, the system includes an adjustable aperture, or confocal iris 240, that can be adjusted along the x, y and z axes as well as the diameter to vary the field of view and depth information. The adjustment of the aperture 240 can be electronically controlled by a translation stage receiving a correction signal that is sent out by a processor on the basis of wavelength information collected by the detector.

With reference to FIG. 2, light is directed from a laser source (SDL-XC30) 200 to a periscope 202, then through a 4 meter lens 204, a half-wave plate 206, in iris 208, a metal/dielectric filter 210, a holographic bandpass filter 212, a second periscope 214, a second half-wave plate 216, a second iris 218, a series of three mirrors 220, 222, 224, and a focusing lens 226, before arriving at the tissue, which is positioned in the sample holder 228 (tissue modulation device). Light emitted by the tissue passes through a camera lens 230 and on to a pellicle 232, which directs some of the light to a CCD imaging camera 236 after passing through a lens 234. The remaining light from the tissue is directed through a second camera lens 238, a confocal iris 240, a third camera lens 242, a polarizer 244, a holographic notch filter 246, and a fourth camera lens 248, before the light enters the holographic spectrograph 250 having a light collection efficiency of f=1.4, to which is coupled a CCD detector 252.

Wavelength Stabilization

In recent years, near infrared lasers have become increasingly attractive as excitation sources for Raman spectrometers. Because of their high continuous wave (CW) powers, small size, relatively low cost, mass manufacturability and ability to produce Raman spectra across the region of maximum sensitivity of silicon based detectors, such lasers have many ideal properties as Raman excitation sources. Near infrared lasers are particularly well-suited to biomedical applications because of their overlap with the spectral region of minimum absorbance and maximum transmission through human tissues.

Various schemes are utilized to minimize laser bandwidth and maximize power. Incorporation of the laser diode into an external resonant cavity produces, in many respects, a nearly ideal excitation source at the expense of increasing size, cost and optomechanical complexity. It would be advantageous for many applications to be able to reduce the cost, physical complexity, and size of the excitation source.

No matter what scheme is employed, diode lasers require some form of external temperature stabilization. Thermally induced cavity length variation causes a corresponding variation of the output wavelength. Thermistor and thermocouple sensors are typically employed in combination with thermoelectric transducers to monitor and actively stabilize the temperature of diodes. The ability to regulate the temperature limits the ability to stabilize the wavelength and amplitude.

Averaging Raman spectra collected over periods of time exceeding the time required for the laser output wavelength to drift a typical amount results in an effective loss of spectral resolution. That is, wavelength stabilization based on independent temperature stabilization is barely adequate for certain Raman based applications because some of the spectral bandwidth and the residual wavelength fluctuations can exceed the difference in small Raman shifts. The independent temperature based approach requires recalibration as the diode and transducers age and their characteristics change, e.g. the relation between output wavelength and temperature drifts. Having a method and apparatus for maintaining wavelength stability in the excitation source that drifts with the laser as it ages would increase the useful lifetime of the laser.

One could simply insert some type of internal standard into the optical system that generated a Raman signal that could be used for feedback to stabilize the excitation wavelength or amplitude. However, for many biomedical applications requiring a small, inexpensive, portable Raman based, near infrared monitoring device, as well as those using larger, nonportable devices, one cannot easily incorporate extra detectors or wavelength collection and analysis hardware due to the increase in system overhead. Even if a separate detector must be used, a simple, inexpensive detector with an optical system of minimal complexity is desirable. The invention provides a stabilization method in which a Raman signal is derived from a material that must be in the optical train for other reasons. For example, certain glass optical elements generate both fluorescence and Raman signals that can be used for stabilization.

Monitoring the strong, spectrally sharp Raman signal of silica at about 1003 $cm^{-1}$ produces an excellent feedback signal for wavelength and amplitude stabilization. The strength and appearance of this signal is correlated with the laser wavelength and the laser amplitude. A window or lens can be used in the optical train that produces a strong silica Raman band, but low fluorescence, such as Corning HPFS 7940 or 7980. For example, from the excitation focusing lens, wavelength stabilization and amplitude stabilization information can be extracted using either the same multichannel detector as is used to collect the sample Raman signals, in the context of a multichannel device, or, in the context of a small portable instrument, by including one more single channel detectors and one or more appropriate filters.

Another solution is to utilize the Raman signal from the samples themselves. Consideration must be given to what types of signals are sought. In the case of noninvasive spectroscopic probing of in vivo human tissue, there will always be signals from the tissues themselves that can be used. In particular, the stratum corneum is the source of a strong Raman feature at 1650–1670 $cm^{-1}$ due to the proteins keratin, elastin and collagen. This signal is typically about as broad spectrally as a multimode diode laser output, 50 $cm^{-1}$, and is sufficiently strong to allow easy collection of sufficient signal to provide the necessary feedback. Perhaps the best Raman feature for this purpose is the 2900–3000 $cm^{-1}$ feature attributable to C—H stretching vibrations.

A method for using this Raman signal as feedback for wavelength stabilization comprises illuminating the tissue with a focussed beam of diode laser radiation at wavelength $\lambda$. This produces scattered radiation that is gathered by a collection lens and directed to an entrance of a detection system. The detection system counts the number of Raman shifted photons for a period of time, called the "counting period". In the context of a multichannel apparatus, the scattered radiation is passed through a spectrograph, which disperses the radiation across the detector face (e.g., CCD) producing a set of scattered wavelength shifted photon counts as a function of wavelength shift. In the context of a single channel detector, the collected photons are passed through a filter that transmits only photons in the appropriate wavelength shifted spectral region, and these are detected by a detector like an avalanche photodiode, a photomultiplier or possibly in some cases even a PIN diode. Before an automated feedback cycle begins, the entire system Chaser wavelength, detection characteristics, positions of excitation focusing lens and scattered radiation collection lens) is viewed as manually configured to produce an optimal signal.

The multichannel detector controller (computer) is programmed to automatically compare the number of shifted photons, e.g., at a Raman shift of 2950 $cm^{-1}$, with the number obtained (at the same shift) during the previous counting period. If the number is the same, within a present tolerance range, then the controller sends a signal to the thermoelectric cooler to maintain the same temperature. If the number has decreased, then the controller sends a different electronic signal to the thermoelectric cooler associated with the diode excitation laser. This electronic signal causes the cooler to increase or decrease its cooling. If, at the end of the next period, the number of shifted photons at a Raman shift of 2950 $cm^{-1}$ is less than the number before, then the diode temperature was not adjusted in the correct direction (i.e. made too cold or too hot) and a signal is sent out to decrease or increase the cooling, as appropriate. At the end of the next counting period, the photon numbers are compared again, and if the number is increasing, then the direction of cooling or heating is maintained until a subsequent counting period produces the same or a decreased signal.

The cycle delineated above can be continued for as long and as often as one cares to make measurements. The amount of the cooling/heating signal sent to the thermoelectric device can be either a direct comparison of Raman counts from counting during successive periods, i.e. the "derivative" signal itself, or it can be proportional to both the difference between the counts obtained in successive counting periods and the difference between the two succeeding differences (i.e. the second derivative). In this way, it is possible to maintain the wavelength and amplitude stability of a less expensive and bulky laser system using the Raman signals themselves for feedback.

Focusing and Collection Lenses

Similarly, it is possible to maintain the orientation and alignment of the collection and excitation lenses 120, 116 in the optical system 100 as the subject moves, or as other factors in the measurement system change. In this case, the feedback is again derived directly from the Raman signals as above (derivatives or second derivatives), but now the positions of the two lenses 116, 120 are adjusted to obtain a stable signal. The feedback signal can be fed to translation stages that control the position of each lens independently. Assuming an actively wavelength and amplitude stabilized laser system, e.g., utilizing the method described above, one monitors a Raman feature that can be easily observed and can be identified with a specific layer of the tissue in question, such as stratum corneum, epidermis, or dermis. These features occur in the C—H stretching region, i.e. 2920–3100 $cm^{-1}$ or in the protein regions, i.e. 1645 $cm^{-1}$, associated with keratin, elastin, collagen, or in the 1445 $cm^{-1}$ region, associated with fats, i.e. adipose tissue.

Wavelength adjustments and lens position adjustments can occur in any order, but not simultaneously. That is, since the wavelength stability is independent of the spatial adjustments, it is necessary to optimize the diode properties for the positions of the two lenses being constant. After diode wavelength and amplitude stabilization is complete (for at least one cycle, all other factors being constant), then the processor can perform the lens and aperture adjustments.

Two exemplary situations in which the methods and apparatus of the invention are applicable include a biopsy situation and a scanning situation. In the first situation, the sample of interest is being biopsied for a particular type of tissue. In this case, an optimal position for the lens system is sought as the sample is moved in the directions perpendicular to the excitation optical axis (x, y) to sample the Raman activity. The task is to search for or "lock onto" a particular type of activity indicative of a diseased tissue or a particular depth or layer of tissue that is held constant as the sample is moved in the directions perpendicular to the optical axis of the excitation light. For example, this approach can be useful for differentiating between basal cell carcinoma (deeper cells or layers) and malignant melanoma (surface cells).

In the other situation, the positions of the tissue perpendicular to the optical axis of the excitation light are held constant while scanning in the direction along the optical axis (z) of the excitation light. That is, the position of the excitation laser focusing lens is moved incrementally, and the collection lens is then adjusted after each incremental movement of the focusing lens. This generates a "depth profile" with regard to a particular type of tissue. The lens adjustments made in this process are not independent. Regardless of the position of the collection optics, Raman signal can only come from the region sufficiently illuminated by the excitation laser. It therefore makes sense to initiate any search/mapping/locking algorithm with some incremental movement of the excitation lens.

In each case, the optimization will find the relative position of the two lenses that maximizes the Raman feature of interest (or in a multichannel environment, maximizes some feature(s) while minimizing others, as in the differentiation of dermis from epidermis and stratum corneum based on the C—H stretching region). In a single channel environment, a filter/detector can be used for obtain information related to each feature of interest. In a multichannel environment, the different features can be observed using a spectrograph, within the limits of dispersion. The optimal position of the collection lens relates not only to the propagation of the excitation laser into the inhomogeneous tissues but also to the propagation of the Raman scattered radiation out of the illuminated region. These issues relate to various aspects of the tissue including types and degree of spatial and optical inhomogeneity in and near the region of interest.

For sampling (x, y axes) over relatively small regions, having a characteristic size of about a few millimeters to a few centimeters or depths (z axis) of microns up to a millimeter or so, and relatively flat tissues, (back, neck, even finger tips over small enough regions, such as a millimeter or two in the x-y direction), one can model the radiation propagation through the tissue and thereby relate the variation of the strength of the Raman features with either the variation of tissue characteristics with depth or the relative variation of tissue type as the "Raman biopsy" is scanned parallel across the surface of the skin. This latter characterization can either be at a constant depth with regard to the surface or simply a measure of maximum amount of tissue type variation across the direction(s) parallel to the skin surface (line scan or surface map). Characterization at a constant depth that shows fluctuations is indicative of wrinkles.

In either case, one lens adjustment (excitation is varied first either in response to motion of the sample or in response to the desire to illuminate a different depth of tissue in question) must be followed by the system finding the optimal position of the other lens, i.e. the collection lens. This will tend to find the best overlap between the collection and excitation cones with regard to the tissues producing the Raman signal of interest. Thus the system allows a search of the tissues with optimal overlap of the excitation and collection systems.

Methods

The invention provides a method for obtaining spectroscopic information from living tissue of a subject. In one embodiment, the method comprises irradiating a tissue of interest in a subject with light passing from a light source through a first adjustable lens, and passing spectra that are emitted by the tissue through a second adjustable lens. The spectra that are passed through the second adjustable lens are then collected and analyzed to determine a target signal associated with an analyte of interest. The method further comprises deriving a correction signal from the target signal based on comparing the new target signal with a target signal associated with a previous counting period, and adjusting the position of the first adjustable lens or the second adjustable lens and/or an adjustable aperture on the basis of the correction signal so as to enhance the target signal.

In a preferred embodiment for obtaining feedback based on static tissues, the spectra are Raman spectra. However, in an embodiment based on probing mobile tissues (e.g., blood), use of visible fluorescence is preferred. In this case, a preferred excitation wavelength is in the range of about 580–680 nm. The method can optionally further comprise selectively dispersing a target wavelength of the collected spectra prior to analyzing the collected spectra. Preferably, the dispersing comprises filtering out wavelengths other than the target wavelength, or passing the collected spectra through a spectrograph.

Examples of excitation wavelengths include, but are not limited to, about 785, 805, 808, 830, and 850 nm. Examples of target wavelengths include, but are not limited to, Raman shifts of about 529–556, 811–830, 938, 1087–1101, 1245, 1269, 1297, 1445, 1650–1670, 2100–2200, 2852, 2883, 2933, 2935, 2944, 2987, and 2850–3000 $cm^{-1}$. Examples of analytes include, but are not limited to, phosphorous-containing bonds, carbon-hydrogen bonds, carbon-deuterium bonds, amide linkages, moisture, nucleic acid (DNA, RNA), protein, lipid, carbohydrate, collagen, elastin and keratin.

In another aspect, the invention provides a non-invasive method for spectroscopically probing a target layer of skin in a subject. The method comprises irradiating a target layer of skin in a subject with light having an excitation wavelength that passes from a light source through a first adjustable lens, passing spectra that are emitted by the tissue through a second adjustable lens and/or an adjustable aperture, and collecting spectra that are passed through the second adjustable lens and/or aperture. The method further comprises analyzing the collected spectra to determine a target signal associated with the target layer of skin, and adjusting the position of the first adjustable lens, the second adjustable lens, and/or the adjustable aperture so as to increase the target signal. Optionally, the method further comprises deriving a correction signal from the target signal and relaying the correction signal to the first adjustable lens, the second adjustable lens and/or the adjustable aperture, wherein the correction signal effects an adjustment of the first adjustable lens or the second adjustable lens.

In another aspect, the invention provides a method for detecting abnormalities in living tissue of a subject. The method comprises irradiating a tissue of interest in a subject with light passing from a light source through a first adjustable lens, passing spectra that are emitted by the tissue through a second adjustable lens and/or an adjustable aperture, and collecting spectra that are passed through the second adjustable lens and/or aperture. The method further comprises analyzing the collected spectra to determine a target signal associated with a tissue feature indicative of an abnormality, deriving a correction signal from the target signal, and adjusting the position of the first adjustable lens, the second adjustable lens and/or the adjustable aperture on the basis of the correction signal so as to enhance the target signal. In one embodiment, the tissue of interest comprises skin. Other examples of tissues of interest include, but are not limited to, stratum corneum, epidermis, intradermal capillary beds, and dermis.

Abnormalities that can be detected include, but are not limited to, various cancers, genetic disorders such as so-called "elephant skin", psoriasis, and other conditions related to imbalances of lipid, protein, carbohydrate and water content. Cancers can be detected, for example, by detecting increases in phosphorous-containing bonds, as are abundant in nucleic acids such as DNA and RNA, and by detecting changes in morphology and tissue density. Because metabolites are excreted to a significant extent via the sweat glands, the process can be used to detect substances that an individual has ingested. In addition, one can discriminate between substances that find their way onto the skin from exogenous sources as opposed to from endogenous sources. It is therefore possible to use the method to serve as a forensic or security tool. Such a tool would also reveal individuals who have handled guns or bomb making materials, drugs or drug making chemicals or who have ingested certain foods or substances.

The invention further provides a method for stabilizing a wavelength of light emitted by a diode laser. This stabilization of the wavelength will also stabilize amplitude. The method comprises irradiating a specimen with excitation light from the diode laser, and collecting Raman spectra at a target wavelength emitted by the irradiated specimen, wherein the target wavelength is associated with a strong feature in the specimen. In one embodiment, the target wavelength is associated with silica, as present in the optical path, such that an optical element within the system serves as the irradiated specimen. The target wavelength associated with silica is a wavenumber shift of about 1003 cm$^{-1}$ from the excitation wavelength. The method further comprises determining a quantity of spectra emitted at the target wavelength, relaying to the diode laser a signal proportional to the determined quantity, and regulating the temperature of the diode laser so as to maintain a maximal spectra emitted at the target wavelength.

Figure 3:
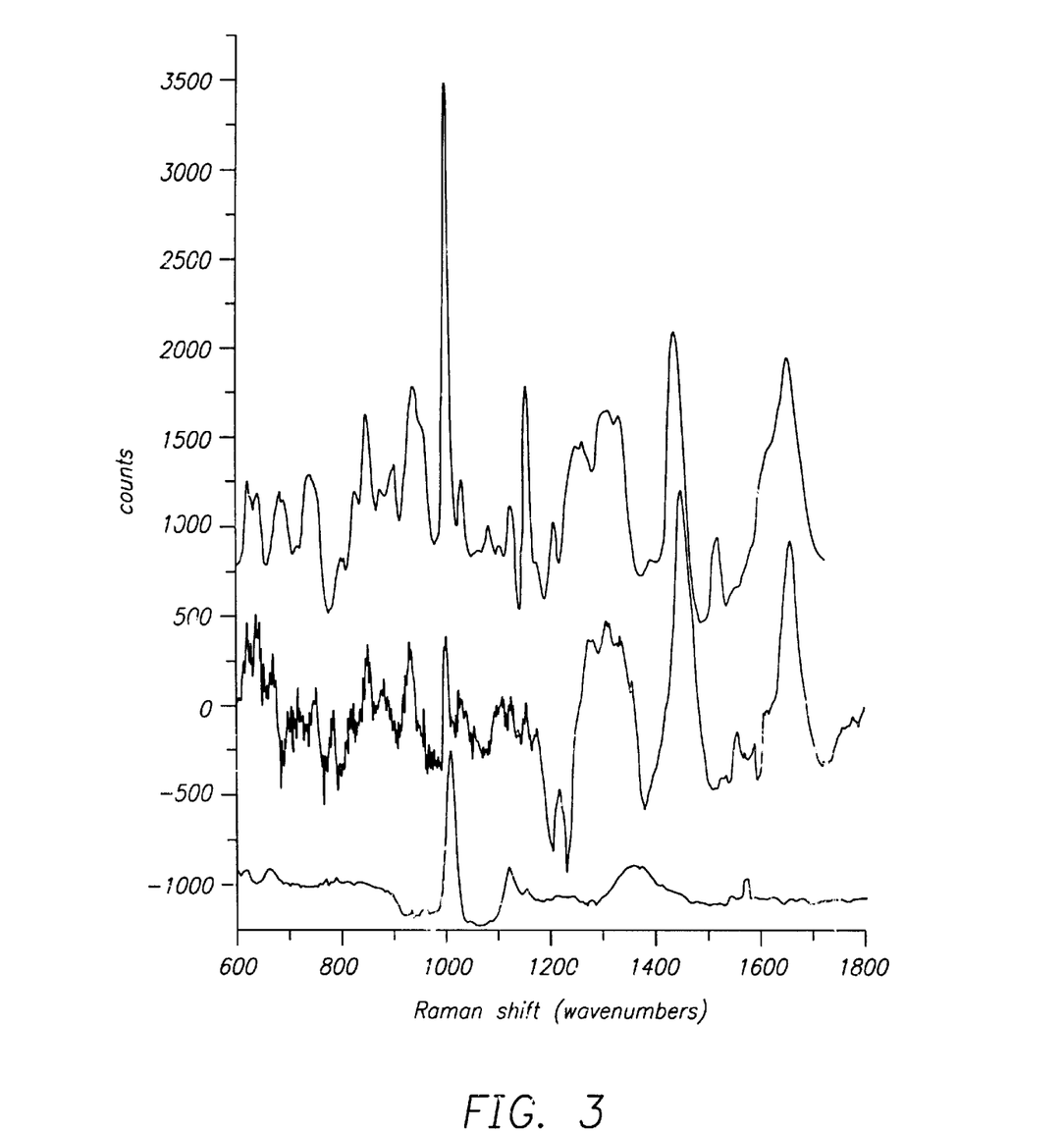
FIG. 3 is a plot of background-corrected spectral counts at wavenumber shifts of 600–1800 for 3 different samples: an in vitro blood sample; an in vivo blood sample; and a NaCl pellet.

FIG. 3 shows spectral counts obtained at Raman shifts of about 600–1800 wavenumbers and revealing a peak associated with silica at 1003 cm$^{-1}$. The lower trace was obtained from a pellet of NaCl, and the middle trace from an in vivo non-invasive probing of blood in a human subject using equipment and methods as described herein. The upper trace is from Koo et al., 1999, Diabetes Tech. Ther. 1:153–157, and was taken from an in vitro sample of whole blood using fiber optics. The silica peak at 1003 cm$^{-1}$ appears consistently in all three conditions, including the NaCl pellet, confirming that this peak is indeed attributable to silica in the optical path.

In another embodiment, Raman spectra are collected at two wavelengths: a positive target wavelength associated with a strong feature in the specimen, and at a negative target wavelength associated with a weak feature in the specimen. The method further comprises determining a quantitative difference between the spectra emitted at the positive target wavelength and the spectra emitted at the negative target wavelength, relaying to the diode laser a signal proportional to the determined difference, and regulating the temperature of the diode laser so as to maintain a maximal difference between the spectra emitted at the positive target wavelength and the spectra emitted at the negative target wavelength.

In a preferred embodiment, the specimen is skin, the positive target wavelength is a wavenumber shift of about 2940 or 1665 cm$^{-1}$ from the excitation wavelength and the negative target wavelength is a wavenumber shift of about 2800 or 1775 cm$^{-1}$, respectively, from the excitation wavelength. The method can be used to differentiate between dermis, epidermis and stratum corneum. In this approach, the positive target wavelength is associated with the layer of interest and the negative target wavelength is associated with a layer to be distinguished from the layer of interest. For dermis, a positive target wavelength is a wavenumber shift of about 856, 938, 1245, 1269 or 2987 cm$^{-1}$ from the excitation wavelength, and a negative target wavelength is a wavenumber shift of about 1130, 1297 or 2852 cm$^{-1}$ from the excitation wavelength. For epidermis, a positive target wavelength is a wavenumber shift of about 2933 cm$^{-1}$ from the excitation wavelength, and a negative target wavelength is a wavenumber shift of about 856, 938, 2987 or 2990 cm$^{-1}$ from the excitation wavelength. For stratum corneum, a positive target wavelength is a wavenumber shift of about 1297, 2852 or 2883 cm$^{-1}$ from the excitation wavelength, and a negative target wavelength is a wavenumber shift of about 2987 cm$^{-1}$ from the excitation wavelength.

The method can be performed non-invasively on living tissue. Optionally, the method further comprises adjusting the position of a first adjustable lens located in the optical path of the excitation light so as to increase the determined difference between the spectra emitted at the positive target wavelength and the spectra emitted at the negative target wavelength, and/or adjusting the position of a second adjustable lens and/or an adjustable aperture located in the optical path of the emitted spectra so as to increase the determined difference between the spectra emitted at the positive target wavelength and the spectra emitted at the negative target wavelength.

In another embodiment, the invention provides a method for assessing the aging of skin and related tissues. The method comprises characterizing the content of the skin using Raman spectroscopy as described above. In one embodiment, the collagen, elastin, and or keratin content of the skin is characterized, as is the spatial mapping of wrinkles.

Flow Charts

Figure 4:
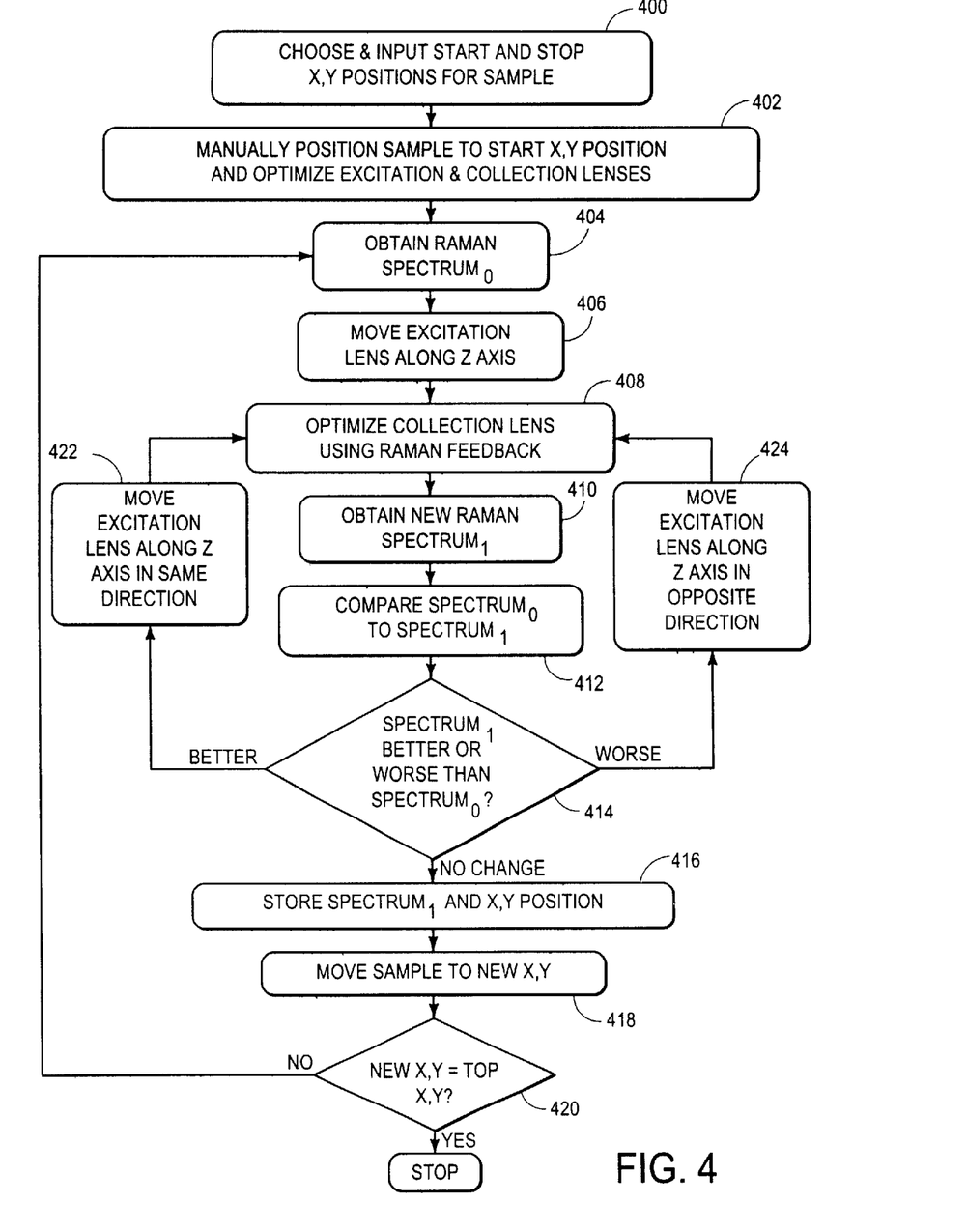
FIG. 4 is a flow chart representing a scanning method according to the invention.

FIG. 4 is a flow chart showing the logic involved in performing a scan of tissue in the x-y dimensions. At box 400, start x, y and stop x, y positions for the sample are chosen and input to a computer. At box 402, the sample is manually positioned to the start x, y position and the excitation and collection lens positions are manually optimized. At box 404, a Raman spectrum$_0$ is obtained. At box 406, the excitation lens is moved in or out, in a direction along the z axis. Then the collection lens position is optimized using Raman feedback at 408, and a new Raman spectrum$_1$ is obtained at 410. At box 412, spectrum$_0$ is compared to spectrum$_1$. Box 414 is a decision box. If the new spectrum is better, control moves to box 422, with movement of the excitation lens in the same direction as previously, and then returns to box 408. If the new spectrum is worse, control moves to box 424, with movement of the excitation lens in the opposite direction as previously, and then returns to box 406. If no change, within a preset tolerance, is detected at decision box 414, control moves to box 416, where Raman spectrum data and the x, y position are stored. At box 418, the sample is automatically moved to a new x, y position. Box 420 is a decision box. If the new x, y is not equal to the stop x, y, then control returns to box 404. If the new x, y is equal to the stop x, y, then the process stops. It is understood that variation of the size of incremental spatial adjustments of lenses and apertures are made in accordance with preset tolerances so as to yield optimized conditions in a reasonable number of iterations and with a minimal number of oscillations.

Figure 5:
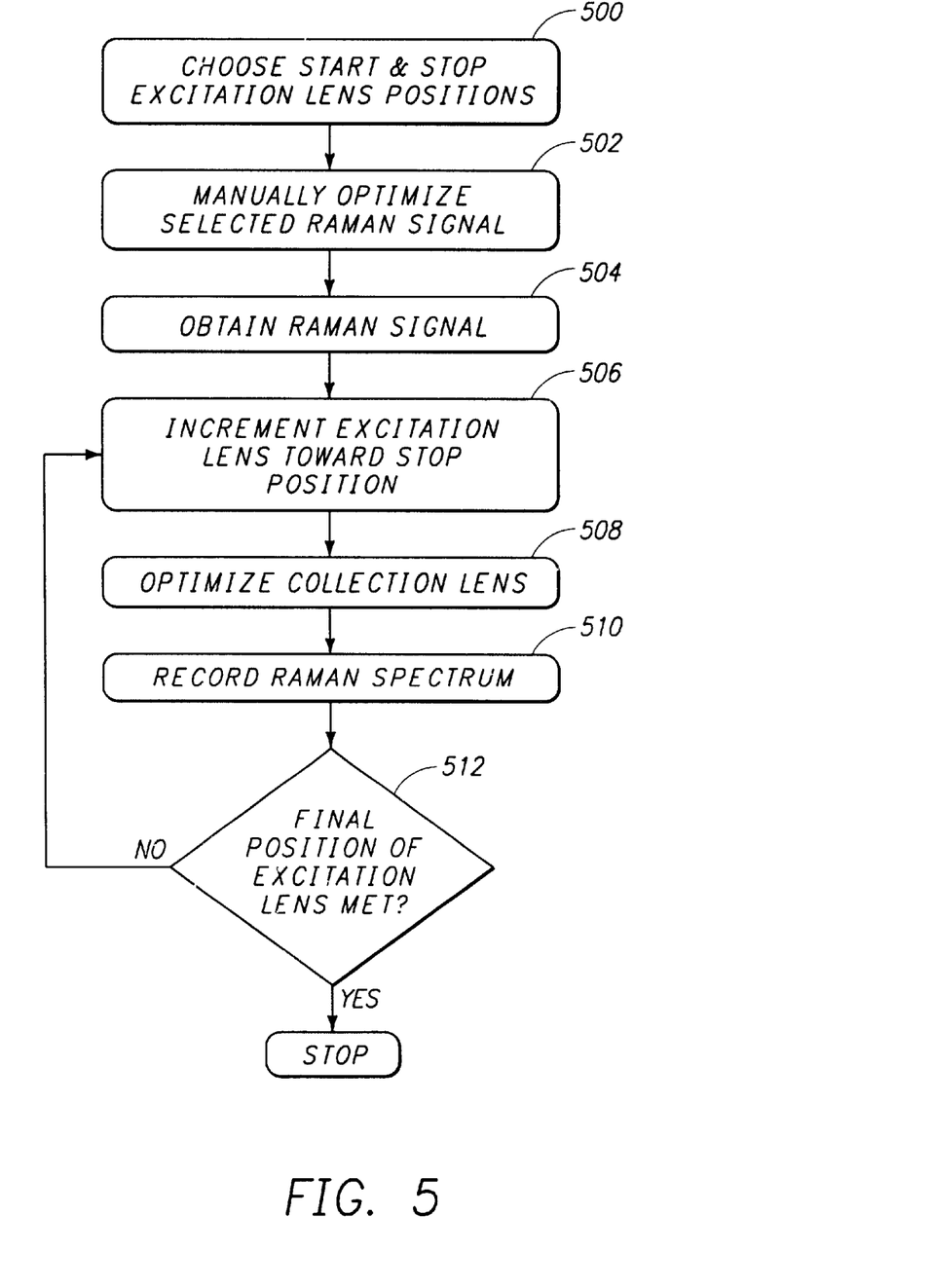
FIG. 5 is a flow chart representing a depth profiling method according to the invention.

FIG. 5 is a flow chart showing the logic involved in obtaining a depth profile. At box 500, the start and stop excitation lens positions are chosen. At box 502, the selected Raman signal is manually optimized. At box 504, a Raman signal is obtained. Then, the position of the excitation lens is moved in an increment toward the stop position at 506. At box 508, the collection lens position is optimized. The Raman spectrum is recorded at box 510. Box 512 is a decision box. If the final position of the excitation lens has not been met, control returns to box 506. If the final position has been met, the process stops.

Those skilled in the art will appreciate other variations and modifications that can be adapted for the methods and apparatus disclosed herein without departing from the spirit and scope of the invention.

What is claimed is:

1. A method for stabilizing a wavelength of light emitted by a diode laser comprising:
   (a) irradiating a specimen with excitation light from the diode laser;
   (b) collecting Raman spectra at a positive target wavelength and at a negative target wavelength emitted by the irradiated specimen, wherein the positive target wavelength is associated with an abundant feature in the specimen and wherein the negative target wavelength is associated with a scant feature in the specimen;
   (c) determining a quantitative difference between the spectra emitted at the positive target wavelength and the spectra emitted at the negative target wavelength;
   (d) relaying to the diode laser a signal proportional to the determined difference; and
   (e) regulating the temperature of the diode laser so as to maintain a maximal difference between the spectra emitted at the positive target wavelength and the spectra emitted at the negative target wavelength.

2. The method of claim 1, wherein the specimen is skin.

3. The method of claim 1, wherein the positive target wavelength is a Raman shift of about 1640 $cm^{-1}$ and the negative target wavelength is Raman shift of about 1720 $cm^{-1}$ relative to the excitation light.

4. The method of claim 1, wherein the specimen is living tissue and the method is performed noninvasively.

5. The method of claim 1, further comprising adjusting the position of a first adjustable lens located in an optical path of the excitation light so as to increase the determined difference between the spectra emitted at the positive target wavelength and the spectra emitted at the negative target wavelength.

6. The method of claim 1, further comprising adjusting the position of a second adjustable lens located in an optical path of the emitted spectra so as to increase the determined difference between the spectra emitted at the positive target wavelength and the spectra emitted at the negative target wavelength.

7. An apparatus for enhancing spectroscopic information from living tissue of a subject comprising
   (a) a diode laser for irradiating a specimen with excitation light from the diode laser;
   (b) detector means fir collecting Raman spectra at a positive target wavelength and at a negative target wavelength emitted by an irradiated specimen, wherein the positive target wavelength is associated with an abundant feature in the specimen and wherein the negative target wavelength is associated with a scant feature in the specimen;
   (c) processor means for determining a quantitative difference between the spectra emitted at the positive target wavelength and the spectra emitted at the negative target wavelength;
   (d) means for relaying to the diode laser an output signal proportional to the determined difference; and
   (e) means for regulating the temperature of the diode laser so as to maintain a maximal difference between the spectra emitted at the positive target wavelength and the spectra emitted at the negative target wavelength, wherein the output signal regulates the temperature of the diode laser, thereby stabilizing the wavelength or amplitude of light emitted by the diode laser.

8. The apparatus of claim 7, further comprising an adjustable lens connected to the processor means and optically aligned with an output path from the laser, wherein the output signal regulates movement of the adjustable lens along an optical axis aligned with the output path of the laser.

9. The apparatus of claim 8, further comprising an electronically controlled translation stage coupled to the adjustable lens for receiving an output signal from the processor means.

10. The apparatus of claim 7, further comprising an adjustable lens connected to the processor means and optically aligned with an input path to the detector means, wherein the output signal regulates movement of the adjustable lens along an optical axis aligned with the input path of the detector means.

11. The apparatus of claim 10, further comprising an electronically controlled translation stage coupled to the adjustable lens for receiving en output signal from the process or means.

12. The apparatus of claim 7, further comprising an adjustable aperture coupled to an electronically controlled translation stage that is connected to the processor means and optically aligned with an input path to the detector means, wherein the output signal regulates movement or diameter of the adjustable aperture along or perpendicular to an optical axis aligned with the input path of the detector means.

* * * * *

UNITED STATES PATENT AND TRADEMARK OFFICE
CERTIFICATE OF CORRECTION

PATENT NO. : 6,681,133 B1
DATED : January 20, 2004
INVENTOR(S) : Joseph Chaiken, Charles M. Peterson and Karen P. Peterson

It is certified that error appears in the above-identified patent and that said Letters Patent is hereby corrected as shown below:

Column 17,
Line 22, after "a" insert -- tissue --.

Column 18,
Line 2, after "comprising" insert -- : -- (semicolon).
Line 5, "fir" should read -- for --.
Line 43, "en" should read -- an --.
Line 44, "process or" should read -- processor --.

Signed and Sealed this

Eighth Day of June, 2004

JON W. DUDAS
*Acting Director of the United States Patent and Trademark Office*